US007879892B2

(12) United States Patent
Macherla et al.

(10) Patent No.: US 7,879,892 B2
(45) Date of Patent: Feb. 1, 2011

(54) ANTI-CANCER AND ANTI-MICROBIAL OXAZOLIDINONES

(75) Inventors: Venkata Rami Reddy Macherla, San Diego, CA (US); Benjamin Nicholson, Narbeth, PA (US); Kin Sing Lam, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 230 days.

(21) Appl. No.: 12/124,909

(22) Filed: May 21, 2008

(65) Prior Publication Data
US 2008/0221183 A1    Sep. 11, 2008

Related U.S. Application Data

(62) Division of application No. 11/358,961, filed on Feb. 21, 2006, now Pat. No. 7,378,530.

(60) Provisional application No. 60/655,605, filed on Feb. 22, 2005.

(51) Int. Cl.
*A61K 31/42* (2006.01)
*C07D 277/02* (2006.01)
(52) U.S. Cl. .................. 514/376; 548/182; 548/187
(58) Field of Classification Search .................. 514/376; 548/182, 187
See application file for complete search history.

(56) References Cited

U.S. PATENT DOCUMENTS

| 2,915,527 | A | 12/1959 | Campbell et al. |
|---|---|---|---|
| 2,971,958 | A | 2/1961 | Lynn |
| 3,129,222 | A | 4/1964 | Bicking |
| 3,182,063 | A | 5/1965 | Satzinger et al. |
| 4,049,816 | A | 9/1977 | Harnden et al. |
| 4,584,385 | A | 4/1986 | Dirlam |
| 4,629,794 | A | 12/1986 | Dirlam |
| 4,650,512 | A | 3/1987 | Felix et al. |
| 4,769,232 | A | 9/1988 | Chappel et al. |
| 6,387,687 | B1 | 5/2002 | Naotsuka et al. |
| 7,378,530 | B2 | 5/2008 | Macherla et al. |
| 2008/0221183 | A1 | 9/2008 | Macherla et al. |

FOREIGN PATENT DOCUMENTS

| DE | 1916715 | 10/1970 |
|---|---|---|
| DE | 1966053 | 4/1971 |
| WO | WO 98/22450 | 5/1998 |

OTHER PUBLICATIONS

Office Action dated Jul. 18, 2007 from U.S. Appl. No. 11/358,961, filed Feb. 21, 2006.
Notice of Allowance dated Jan. 16, 2008 from U.S. Appl. No. 11/358,961, filed Feb. 21, 2006.
Abell et al., "Chemistry of the Mycalamides: Antiviral and Antitumour Compounds from the New Zealand Marine Sponge. Part 6. The Synthesis and testing of analogues of the C(7)-C(10) Fragment," *J Chem Soc., Perkin Transactions I*, 1647-1654, (1997).
Alm et al., "Effects of Topically Applied PGF and its Isopropylester on Normal and Glaucomatous Human Eyes," *Prog. Clin. Biol. Res.*, 312:447-58, (1989).
Avalos M. et al., "Reactivity of 2-methylthioisomüchnone with Acid Chlorides," *Tetrahedron Letters*, 44(25): 4657-4660, (Jun. 16, 2003).
"Bioreversible Carriers in Drug Design: Theory and Application", ed. E.B. Roche, Pergamon Press: New York, 14-21, (1987).
Bull, A.T. et al., "Search and Discovery Strategies for Biotechnology: the Paradigm Shift," *Microbiol. Mol. Biol. Rev.*, 64(3): 573-606, (2000).
Cragg, G.M. & D.J. Newman, "Chemical Diversity: a Function of Biodiversity," *Trends Pharmacol Sci.* 23:404-405, (2002).
"Design of Prodrugs" (1985) ed. H. Bundgaard, Elsevier.
Fingl et al., "General Principles," *The Pharmacological Basis of Therapeutics*, 5$^{th}$ Ed., Sec. 1, Ch.1, p. 1-46, (1975).
Faulkner, D.J. "Marine Natural Products," *Nat Prod Rep.* 18(1): 1-49, (2001).
Frenz, J.L.. Kohl, A.C. & R.G. Kerr, "Marine Natural Products as Therapeutic Agents: Part 2." *Exp. Opin. Ther. Patents*, 14: 17-33, (2004).
Green and Wuts, *Protective Groups in Organic Synthesis*, 3$^{rd}$ Ed., John Wiley & Sons, New York, NY, (1999).
Gullo et al., "Drug Discovery from Natural Products," *J Ind Microbiol Biotech*, 33: 523-531, (2006).
Higuchi, T., Stella V., "Pro-drugs as Novel Delivery Systems", *American Chemical Society*, A.C.S. Symposium Series, vol. 14, (1975).
Ibrahim et al., "Activated Nitriles in Heterocyclic Synthesis: a Novel Synthesis of Pyrano[2,3-d] pyrimidine, pyrano[2,3-c]pyrazole, pyrano[2,3-d]thiazole & thiazolo[3,2-a]pyridine derivatives," *Indian Journal of Chemistry*, Section B, 26B: 216-219, (1987).
Jagodzinski et al., "Reactions of Secondary β-Ketothioamides with Ethyl Bromoacetate and Ethyl 2-bromopropionate. The Synthesis of N-substituted 2-acylmethylidene-1,3-thiazolidin-4-ones," *Polish Journal of Chemistry*, 74(8): 1101-1114, (2000).
Joshi, A., "Microparticulates for Ophthalmic Drug Delivery," *J. Ocul. Pharmacol.*, 10(1): 29-45, (1994).
Kanamaru, T. et al., "In Vitro and In Vivo Antibacterial Activities of TAK-083, an Agent for Treatment of Helicobacter pylori Infection," *Antimicrobial Agents and Chemotherapy*, 45(9): 2455-2459, (2001).
Kanto, J., "Clinical Pharmacokinetics of Ergotamine, dihydroergotamine, ergotoxine, bromocriptine, methysergide, and lergotrile," *Int. J. Clin. Pharmacol., Ther. Toxicol.*, 21(3): 135-142, (1983).
Kerr, R.G. et al., "Marine Natural Products as Therapeutic Agents," *Exp. Opin. Ther. Patents* 9: 1207-1222, (1999).

(Continued)

Primary Examiner—Rei-tsang Shiao
(74) Attorney, Agent, or Firm—Knobbe, Martens, Olson & Bear LLP

(57) ABSTRACT

Disclosed herein are various novel oxazolidinone, imidazolidinone, and thiazolidinone analogs and methods of treating cancer and/or microbial infection using these analogs. Particular 4-oxazolidinone compounds are shown to have anti-cancer and anti-microbial activity.

18 Claims, No Drawings

OTHER PUBLICATIONS

Larock, R., Comprehensive Organic Transformations, VCH Publishers, (1989).
Mayer et al., "Efficacy of a Novel Hydrogel Formulation in Human Volunteers," Ophthalmologica, 210(2): 101-103, (1996).
Mayer et al., "Marine Pharmacology in 1999: Antitumor and Cytotoxic Compounds," Anticancer Res. 21(4A): 2489-2500, (2001).
Mohareb, R.M., "Phenyl Isothiocyanate in Heterocyclic Synthesis: Novel Synthesis of Thiazoles, Thieno[2,3-b]pyridine, Thiophene and Thieno[3,2-c]pyridazine Derivatives," Monathshefte für Chemie 123: 341-347 (1992).
Moore, B.S.. "Biosynthesis of Marine Natural Products: Microorganisms and Macroalgae," Nat Prod. Rep. 16(6): 653-732 (1999).
Mordenti, "Intraocular Pharmacokinetics and Safety of a Humanized Monoclonal Antibody in Rabbits after Intravitreal Administration of a Solution or a PLGA Microsphere Formulation," Toxicol. Sci., 52(1):101-6, (1999).
Okami, Y. "The Search for Bioactive Metabolites from Marine Bacteria," J Mar Biotechnol. 1: 59-65, (1993).
Paquette, L., Encyclopedia of Reagents for Organic Synthesis, John Wiley and Sons, (1995).
Protective Groups in Organic Chemistry, ed. J.F.W. McOmie, Plenum Press, (1973).
Remington's Pharmaceutical Sciences, 18$^{th}$ Ed., Mack Publishing Co., Easton, PA (1990).
Satzinger, G., "Heterocyclen durch Reaktion von Mercapto- und Hydroxycarbonsäureestern mit aktivierten Nitrilen," Justus Liebigs Annalen der Chemie, 1978(3): 473-511 (1978), Abstract only.
Schach von Wittenau et al., "The structure of Indolmycin,"JACS, 83: 4678-4680, (1961).
Shedden et al., "Efficacy and Tolerability of Timolol Maleate Ophthalmic Gel-Forming Solution Versus Timolol Opthalmic Solution in Adults with Open-Angle Glaucoma or Ocular Hyptertension: A Six-Month, Double-Masked, Multicenter Study." Clin. Ther., 23(3):440-50 (2001).
Smith, S. et al., "The Alkaloids of Ergot. Part 1." J.C.S., 1390-1395, (1930).
"Symposium Drug Discovery From Natural Products," SIM Annual Meeting, Chicago, US, (Aug. 2005).
Van Dormael et al., "Dérivés acylméthyléniques. II. Mérocynanines à Substitution Acylméthylénique," Bulletin Des Societies Chimiques Belges, 57: 364-372, (1948).
Veronese et al., "Base-Promoted Reactions of β-Enaminones with 2-bromo-2-methylpropanamides. Formation of 2-Ketonyloxazolidin-4-ones and Cyclohexanespiro-oxazolidin-4-ones," J Chem Soc. Perkin Transactions I, 781-784, (1984).
Yildirim, I. et al., "Experimental and Theoretical Investigations of Functionalization and Cyclization Reactions of 4-benzoyl-5phenyl1-2,-3-furandione with some acetanilides," Indian J. Chemistry, 36B: 1138-1147, (1997).
Zaleska et al., "Synthesis of 5-substituted Thiazolidine-4-one Derivatives," Pharmazie, 50(8): 537-540, (1995).
Zask et al., "Synthesis of 3-Mercapto-2(5H)-furanones via Reaction of Dilithio-2,4-thiazolidinedione with α-Halo Ketones," Tetrahedron Letters, 34(17): 2719-2722, (1993).
International Search Report for PCT/US2006/006278, Mailed on Dec. 7, 2006.
Office Action dated Jul. 18, 2007 for U.S. Appl. No. 11/358,961, filed Feb. 21, 2006.
USPTO—Office Action, dated Mar. 25, 2010 for U.S. Appl. No. 12/124,896 (NEREUS.106C1).
Wu, et al., Regulatory Perspectives of Type II Prodrug Development and Time-Dependent Toxicity Management: Nonclinical Pharm/Tox Analysis and the role of Comparative Toxicology, 2007, pp. 1-6 vol. 236, Elsevier.

ANTI-CANCER AND ANTI-MICROBIAL OXAZOLIDINONES

RELATED APPLICATIONS

This application is a divisional of U.S. application Ser. No. 11/358,961, filed Feb. 21, 2006, which claims the benefit of U.S. Provisional Application No. 60/655,605, filed on Feb. 22, 2005, both of which are incorporated herein by reference in their entirety.

BACKGROUND

1. Field of the Invention

The present invention relates to the fields of chemistry and medicine. More particularly, the present invention relates to certain oxazolidinone, imidazolidinone, and thiazolidonone analogs and use of those analogs in anti-cancer and anti-microbial pharmaceuticals.

2. Description of the Related Art

Cancer is a leading cause of death in the United States. Despite significant efforts to find new approaches for treating cancer, the primary treatment options remain surgery, chemotherapy and radiation therapy, either alone or in combination. Surgery and radiation therapy, however, are generally useful only for fairly defined types of cancer, and are of limited use for treating patients with disseminated disease. Chemotherapy is the method that is generally useful in treating patients with metastatic cancer or diffuse cancers such as leukemias. Although chemotherapy can provide a therapeutic benefit, it often fails to result in cure of the disease due to the patient's cancer cells becoming resistant to the chemotherapeutic agent. Due, in part, to the likelihood of cancer cells becoming resistant to a chemotherapeutic agent, such agents are commonly used in combination to treat patients.

Similarly, infectious diseases caused, for example, by bacteria are becoming increasingly difficult to treat and cure. For example, more and more microorganisms, such as bacteria, are developing resistance to current antibiotics and chemotherapeutic agents. Examples of such bacteria include both gram positive and gram negative bacteria, including *Staphylococcus, Streptococcus, Mycobacterium, Enterococcus, Corynebacterium, Borrelia, Bacillus, Chlamydia, Mycoplasma*, and the like. Examples of Fungi include *Aspergillus, Candida, Trichoderma*, and the like. Examples of protozoa include *Plasmodium* and *Acanthamoeba*.

Therefore, a need exists for additional chemotherapeutics and antimicrobial agents to treat cancer and infectious disease. A continuing effort is being made by individual investigators, academia and companies to identify new, potentially useful chemotherapeutic and antimicrobial agents.

Marine-derived natural products are a rich source of potential new anti-cancer agents and anti-microbial agents. The oceans are massively complex and house a diverse assemblage of microbes that occur in environments of extreme variations in pressure, salinity, and temperature. Marine microorganisms have therefore developed unique metabolic and physiological capabilities that not only ensure survival in extreme and varied habitats, but also offer the potential to produce metabolites that would not be observed from terrestrial microorganisms (Okami, Y. 1993 *J Mar Biotechnol* 1:59). Representative structural classes of such metabolites include terpenes, peptides, polyketides, and compounds with mixed biosynthetic origins. Many of these molecules have demonstrable anti-tumor, anti-bacterial, anti-fungal, anti-inflammatory or immunosuppressive activities (Bull, A. T. et al. 2000 *Microbiol Mol Biol Rev* 64:573; Cragg, G. M. & D. J. Newman 2002 *Trends Pharmacol Sci* 23:404; Kerr, R. G. & S. S. Kerr 1999 *Exp Opin Ther Patents* 9:1207; Frenz, J. L., Kohl, A. C. & R. G. Kerr 2004 *Exp Opin Ther Patents* 14:17; Moore, B. S 1999 *Nat Prod Rep* 16:653; Faulkner, D. J. 2001 *Nat Prod Rep* 18:1; Mayer, A. M. & V. K. Lehmann 2001 *Anticancer Res* 21:2489), validating the utility of this source for isolating invaluable therapeutic agents. Further, the isolation of novel anti-cancer and anti-microbial agents that represent alternative mechanistic classes to those currently on the market will help to address resistance concerns, including any mechanism-based resistance that may have been engineered into pathogens for bioterrorism purposes.

SUMMARY OF CERTAIN EMBODIMENTS

One aspect of the invention is a compound having the structure of formula I or Ia:

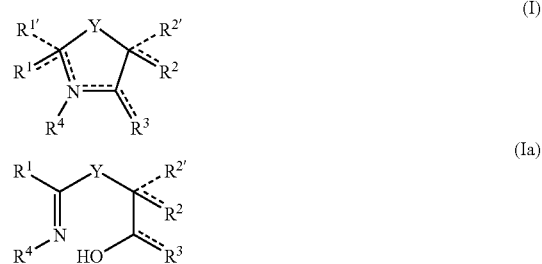

and pharmaceutically acceptable salts or prodrugs thereof, wherein:

$R^1$ and $R^2$ are separately selected, wherein one of $R^1$ and $R^2$ is a molecular fragment having the structure of formula (II),

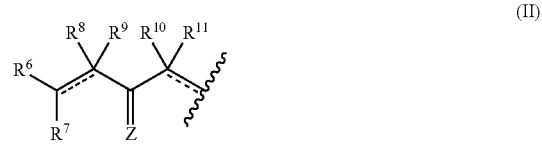

Z is selected from the group consisting of O, S, and $NR^5$;

$R^6$ and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

and the remaining substituent of $R^1$ and $R^2$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^3$ is =O;

$R^{1'}$ and $R^{2'}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

Y is selected from the group consisting of O, S, and $NR^5$;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl, or are separately absent, provided that $R^4$ is not absent in a compound of formula Ia;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

Another aspect of the invention is a compound having the structure of formula III or IIIa:

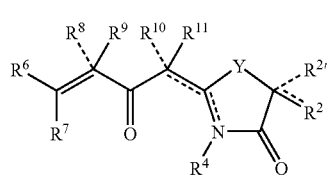

(III)

-continued

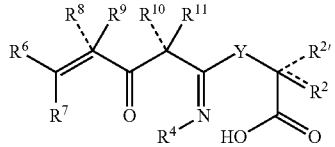

(IIIa)

and pharmaceutically acceptable salts or prodrugs thereof, wherein:

Y is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent, provided that $R^4$ is not absent in a compound of formula IIIa;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

Another aspect of the invention is a compound having the structure of formula IV or IVa:

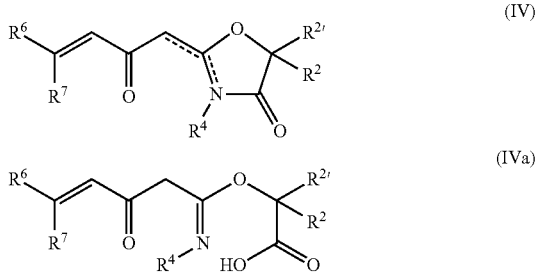

and pharmaceutically acceptable salts or prodrugs thereof, wherein:

$R^2$, $R^6$, and $R^7$ are separately selected from the group consisting of mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl;

$R^{2'}$ is selected from the group consisting of hydrogen and mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl;

$R^4$ is selected from the group consisting of hydrogen, straight- or branched-chain $C_{1-6}$ alkyl, straight- or branched-chain $C_{2-6}$ alkenyl, and straight- or branched-chain $C_{2-6}$ alkynyl, or is absent, provided that $R^4$ is not absent in a compound of formula IVa;

any bond represented by a dashed and solid line represents a bond selected from the group consisting of a single bond and a double bond with the proviso that such bonds in the compound of formula IV may not both be double bonds; and any carbon-carbon double bond has a configuration selected from the group consisting of cis and trans.

Another aspect of the invention is a compound having the structure of formula V or Va:

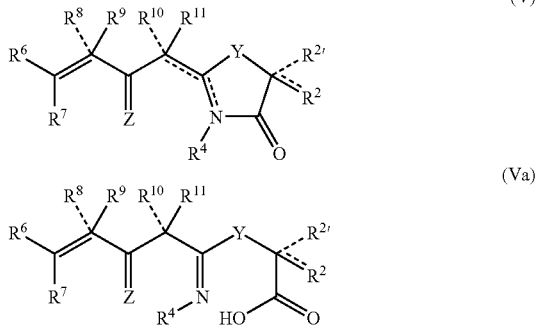

and pharmaceutically acceptable salts or prodrugs thereof, wherein:

Y is selected from the group consisting of O and $NR^5$;

Z is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent, provided that $R^4$ is not absent in a compound of formula Va;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

$R^6$ and $R^8$ are optionally bound together to form an optionally substituted ring;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

Another aspect of the invention is a compound having the structure of formula V or Va:

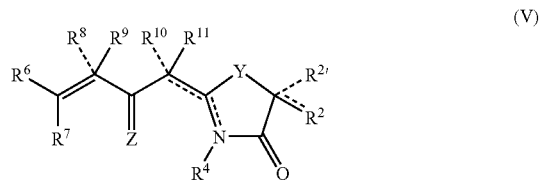

-continued

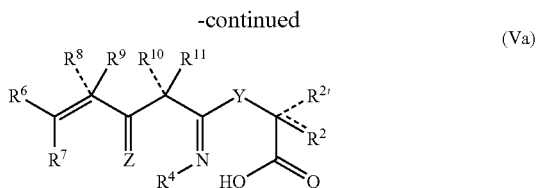

(Va)

and pharmaceutically acceptable salts or prodrugs thereof, wherein:

Y is selected from the group consisting of O, S, and $NR^5$;

Z is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent, provided that $R^4$ is not absent in a compound of formula Va;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

$R^6$ and $R^8$ are optionally bound together to form an optionally substituted ring, provided that if $R^6$ and $R^8$ together form an aryl, then at least one of $R^2$, $R^4$, and $R^{11}$ is not hydrogen;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

Another aspect of the invention is a method of treating an individual infected with a bacterium, comprising: administering to the individual a compound selected from the group consisting of the compounds of formulas I, Ia, III, IIIa, IV, IVa, V, and Va.

Another aspect of the invention is a method of treating an individual with cancer, comprising: administering to the individual a compound selected from the group consisting of the compounds of formulas I, Ia, III, IIIa, IV, IVa, V, and Va.

Another aspect of the invention is a method of treating cancer comprising the step of contacting a cancer cell with a compound selected from the group consisting of the compounds of formulas I, Ia, III, IIIa, IV, IVa, V, and Va.

DETAILED DESCRIPTION OF CERTAIN EMBODIMENTS

In one embodiment, compounds having the structure of formula I are provided:

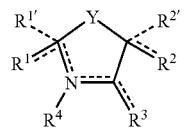

(I)

wherein $R^1$ and $R^2$ are separately selected, and wherein one of $R^1$ and $R^2$ is a molecular fragment having the structure of formula (II),

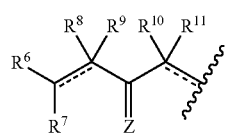

(II)

Z is selected from the group consisting of O, S, and $NR^5$;

$R^6$ and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; arylalkoxy carbonyl; alkoxy carbonylacyl; ester; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; arylalkoxy carbonyl; alkoxy carbonylacyl; ester; amino; aminocarbonyl; amide; aminocarboyloxy; nitro; azido; phenyl; hydroxy; alkylthio; arylthio; oxysulfonyl; carboxy; cyano; and halogenated alkyl including polyhalogenated alkyl; or are separately absent; any bond represented by a dashed and solid line represents a bond selected from the group consisting of a single bond and a double bond;

and the remaining substituent of $R^1$ and $R^2$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl, ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^3$ is =O;

$R^{1'}$ and $R^{2'}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl, ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

Y is selected from the group consisting of O, S, and $NR^5$;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, straight $C_{2-6}$ alkynyl, heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl; or are separately absent;

any bond represented by a single dashed line is a single bond or is absent; and any carbon-carbon double bond has a configuration selected from the group consisting of cis and trans.

It will be appreciated that when a bond represented by a dashed and solid line in the compound of formula I is a double bond, some substituents on the atoms involved in the double bond will be absent and/or other bonds connected to the atoms will be single bonds so that the proper valency of the atoms are not violated. Thus, for example, when the dashed and solid line connected to $R^1$ is a double bond, $R^{1'}$ will be absent and the bond between the nitrogen atom and the carbon atom involved in double bonding with $R^1$ will be a single bond.

In one embodiment, Y and/or Z in the compound of formula I is O. In one embodiment, $R^4$ in the compound of formula I is H. In another embodiment, $R^4$ in the compound of formula I is absent, such as to accommodate a double bond to the nitrogen atom. In some embodiments, $R^8$, $R^9$, $R^{10}$, and $R^{11}$ are separately hydrogen or are separately absent when necessary to accommodate double bonds. In some embodiments, $R^2$ is a mono-substituted, poly-substituted, or unsubstituted variant of $C_1$-$C_{24}$ alkyl. In some embodiments, $R^6$ and $R^7$ are separately mono-substituted, poly-substituted, or unsubstituted variants of $C_1$-$C_{24}$ alkyl.

In one embodiment, the compound of formula I may be subjected to a ring opening reaction to produce the compound of formula Ia:

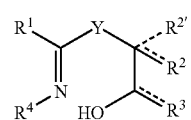

(Ia)

where the substituents are as defined above for formula I, with the proviso that $R^4$ is not absent.

In another embodiment, compounds having the structure of formula III are provided:

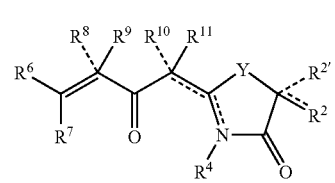

(III)

wherein Y is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; arylalkoxy carbonyl; alkoxy carbonylacyl; ester; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; arylalkoxy carbonyl; alkoxy carbonylacyl; ester; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl; or are separately absent;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; arylalkoxy carbonyl; alkoxy carbonylacyl; ester; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

any bond represented by a dashed and solid line represents a bond selected from the group consisting of a single bond and a double bond; any bond represented by a single dashed line is a single bond or is absent; and any carbon-carbon double bond has a configuration selected from the group consisting of cis and trans.

It will be appreciated that when a bond represented by a dashed and solid line in the compound of formula III is a double bond, some substituents on the atoms involved in the double bond will be absent and/or other bonds connected to the atoms will be single bonds so that the proper valency of the atoms are not violated. Thus, for example, when the dashed and solid line connected to $R^2$ is a double bond, $R^{2'}$ will be absent.

In one embodiment, Y is O in the compound of formula III. In one embodiment, $R^2$ in the compound of formula III is a mono-substituted, poly-substituted, or unsubstituted variant of $C_1$-$C_{24}$ alkyl. In one embodiment, $R^6$ and $R^7$ in the compound of formula III are separately mono-substituted, poly-substituted, or unsubstituted variants of straight chain $C_1$-$C_{24}$ alkyl. In one embodiment, $R^4$ in the compound of formula III is H. In another embodiment, $R^4$ in the compound of formula III is absent, such as to accommodate a double bond to the nitrogen atom. In one embodiment $R^{2'}$ in the compound of formula III is H. In another embodiment, $R^{2'}$ in the compound of formula III is absent, such as to accommodate a double bond. In some embodiments, $R^8$, $R^9$, $R^{10}$, and $R^{11}$ are separately hydrogen or are separately absent when necessary to accommodate double bonds.

In one embodiment, the compound of formula III may be subjected to a ring opening reaction to produce the compound of formula IIIa:

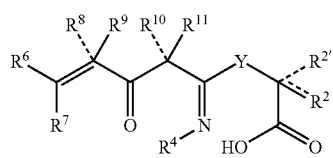

(IIIa)

where the substituents are as defined above for formula III, with the proviso that $R^4$ is not absent.

In another embodiment, a 4-oxazolidinone compound having the structure of formula IV is provided:

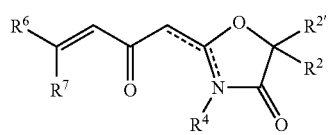

(IV)

wherein $R^2$, $R^6$, and $R^7$ are separately selected from the group consisting of mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl;

$R^{2'}$ is selected from the group consisting of hydrogen and mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl;

$R^4$ is selected from the group consisting of hydrogen, straight- or branched-chain $C_{1-6}$ alkyl, straight- or branched-chain $C_{2-6}$ alkenyl, and straight- or branched-chain $C_{2-6}$ alkynyl, or is absent;

any bond represented by a dashed and solid line represents a bond selected from the group consisting of a single bond and a double bond with the proviso that such bonds in the compound of formula IV may not both be double bonds; and any carbon-carbon double bond has a configuration selected from the group consisting of cis and trans.

It will be appreciated that when a bond represented by a dashed and solid line in the compound of formula IV is a double bond, some substituents on the atoms involved in the double bond will be absent and/or other bonds connected to the atoms will be single bonds so that the proper valency of the atoms are not violated.

In one embodiment, the compound of formula IV may be subjected to a ring opening reaction to produce the compound of formula IVa:

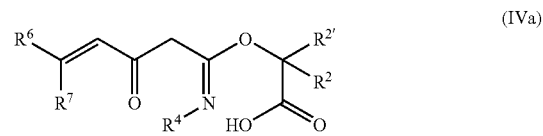

(IVa)

where the substituents are as defined above for formula IV, with the proviso that $R^4$ is not absent.

In one embodiment, $R^2$ in the compound of formula IV is a mono-substituted, poly-substituted, or unsubstituted variant of $C_1$-$C_{24}$ alkyl. In one embodiment, $R^6$ and $R^7$ in the compound of formula IV are separately mono-substituted, poly-substituted, or unsubstituted variants of straight chain $C_1$-$C_{24}$ alkyl. In one embodiment, $R^4$ in the compound of formula IV is H. In another embodiment, $R^4$ in the compound of formula IV is absent, such as to accommodate a double bond to the nitrogen atom. In one embodiment $R^{2'}$ in the compound of formula IV is H. In another embodiment, $R^{2'}$ in the compound of formula IV is absent, such as to accommodate a double bond.

In another embodiment, compounds having the structure of formula V are provided:

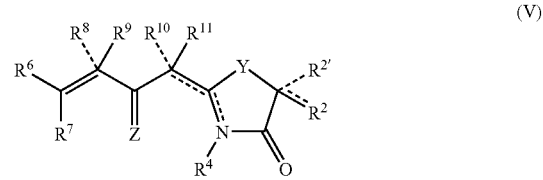

(V)

wherein Y is selected from the group consisting of O, S, and $NR^5$;

Z is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

$R^6$ and $R^8$ are optionally bound together to form an optionally substituted ring;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

In some embodiments, of the compound of formula V, Y is not S. In other embodiments of the compound of formula V, when $R^6$ and $R^8$ together form an aryl, at least one of $R^2$, $R^4$, and $R^{11}$ is not hydrogen.

It will be appreciated that when a bond represented by a dashed and solid line in the compound of formula V is a double bond, some substituents on the atoms involved in the double bond will be absent and/or other bonds connected to the atoms will be single bonds so that the proper valency of the atoms are not violated. Thus, for example, when the dashed and solid line connected to $R^2$ is a double bond, $R^{2'}$ will be absent.

In one embodiment, Y is O in the compound of formula V. In one embodiment, Z is 0 in the compound of formula V. In one embodiment, $R^2$ in the compound of formula V is a mono-substituted, poly-substituted, or unsubstituted variant of $C_1$-$C_{24}$ alkyl. In one embodiment, $R^6$ and $R^7$ in the compound of formula V are separately mono-substituted, poly-substituted, or unsubstituted variants of straight chain $C_1$-$C_{24}$ alkyl. In one embodiment, $R^4$ in the compound of formula V is H. In another embodiment, $R^4$ in the compound of formula V is absent, such as to accommodate a double bond to the nitrogen atom. In one embodiment $R^{2'}$ in the compound of formula V is H. In another embodiment, $R^{2'}$ in the compound of formula V is absent, such as to accommodate a double bond. In some embodiments, $R^8$, $R^9$, $R^{10}$, and $R^{11}$ are separately hydrogen or are separately absent when necessary to accommodate double bonds.

In one embodiment, $R^6$ and $R^8$ in the compound of formula V are bound together to form an optionally substituted aryl. In one such embodiment, the compound of formula V has the structure:

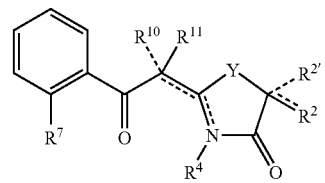

where $R^2$, $R^{2'}$, $R^4$, $R^7$, $R^{10}$, and $R^{11}$ are as defined above.

In one embodiment, the compound of formula V may be subjected to a ring opening reaction to produce the compound of formula Va:

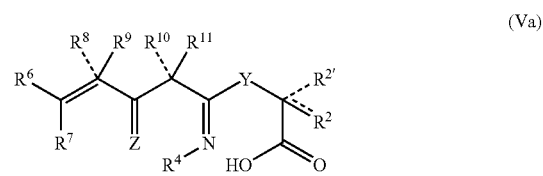

(Va)

where the substituents are as defined above for formula V, with the proviso that $R^4$ is not absent[0027] In one embodiment, the compound of formulas I, III, IV, or V has the structure of formula VI:

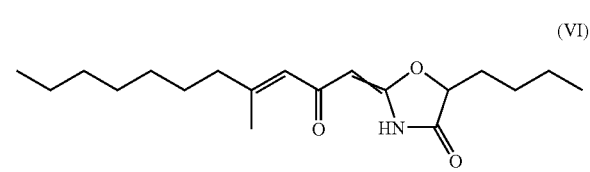

(VI)

wherein the crossed double bond indicates that the double bond may have either a trans or cis geometry.

In another embodiment, the compound of formulas I, III, IV, or V has the structure of formula VII:

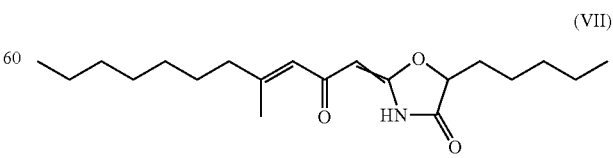

(VII)

wherein the crossed double bond indicates that the double bond may have either a trans or cis geometry.

In another embodiment, the compound of formulas I, III, IV, or V has the structure of formula VIII:

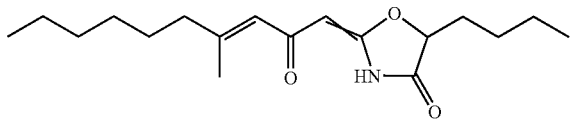

(VIII)

wherein the crossed double bond indicates that the double bond may have either a trans or cis geometry.

In some embodiments, tautomers of the compounds of formulas VI, VII, or VIII are provided. For example, the tautomer of the compound of formula VI having the structure:

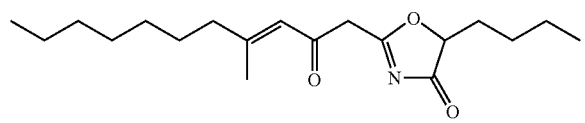

is provided.

In one embodiment, the compound of formulas Ia, IIIa, IVa, or Va has the structure of formula IX:

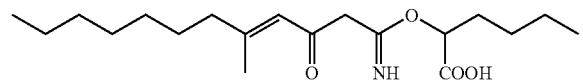

(IX)

In some embodiments, prodrugs, metabolites, stereoisomers, and pharmaceutically acceptable salts of the compounds disclosed herein are provided.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. Conventional procedures for the selection and preparation of suitable prodrug derivatives are described, for example, in *Design of Prodrugs*, (ed. H. Bundgaard, Elsevier, 1985), which is hereby incorporated herein by reference in its entirety.

The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14-21 (1987) (providing examples of esters useful as prodrugs for compounds containing carboxyl groups). Each of the above-mentioned references is herein incorporated by reference in their entirety.

Metabolites of the compounds disclosed herein include active species that are produced upon introduction of the compounds into the biological milieu.

Where the compounds disclosed herein have at least one chiral center, they may exist as a racemate or as enantiomers. It should be noted that all such isomers and mixtures thereof are included in the scope of the present invention. Furthermore, some of the crystalline forms for the compounds of disclosed herein may exist as polymorphs. Such polymorphs are included in one embodiment of the present invention. In addition, some of the compounds of the present invention may form solvates with water (i.e., hydrates) or common organic solvents. Such solvates are included in one embodiment of the present invention.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, phosphoric acid and the like. Pharmaceutical salts can also be obtained by reacting a compound with an organic acid such as aliphatic or aromatic carboxylic or sulfonic acids, for example acetic, succinic, lactic, malic, tartaric, citric, ascorbic, nicotinic, methanesulfonic, ethanesulfonic, p-toluensulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine, lysine, and the like.

If the manufacture of pharmaceutical formulations involves intimate mixing of the pharmaceutical excipients and the active ingredient in its salt form, then it may be desirable to use pharmaceutical excipients which are non-basic, that is, either acidic or neutral excipients.

In various embodiments, the compounds disclosed herein can be used alone, in combination with other compounds disclosed herein, or in combination with one or more other agents active in the therapeutic areas described herein.

The term "halogen atom," as used herein, means any one of the radio-stable atoms of column 7 of the Periodic Table of the Elements, e.g., fluorine, chlorine, bromine, or iodine, with fluorine and chlorine being preferred.

The term "ester" refers to a chemical moiety with formula —(R)$_n$—COOR', where R and R' are independently selected from the group consisting of alkyl, cycloalkyl, aryl, heteroaryl (bonded through a ring carbon) and heteroalicyclic (bonded through a ring carbon), and where n is 0 or 1.

An "amide" is a chemical moiety with formula —(R)$_n$—C(O)NHR', —(R)$_n$—NHC(O)R', —(R)$_n$—C(O)NR'R", or —(R)$_n$,—R'NC(O)R", where R, R', and R" are independently selected from the group consisting of alkyl, cycloalkyl, aryl, heteroaryl (bonded through a ring carbon) and heteroalicyclic (bonded through a ring carbon), and where n is 0 or 1. An amide may be an amino acid or a peptide molecule attached to a molecule of the present invention, thereby forming a prodrug.

Any amine, hydroxy, or carboxyl side chain on the compounds of the present invention can be esterified or amidified. The procedures and specific groups to be used to achieve this end are known to those of skill in the art and can readily be found in reference sources such as Greene and Wuts, Protective Groups in Organic Synthesis, $3^{rd}$ Ed., John Wiley & Sons, New York, N.Y., 1999, which is incorporated herein in its entirety.

The term "aromatic" refers to an aromatic group which has at least one ring having a conjugated pi electron system and includes both carbocyclic aryl (e.g., phenyl) and heterocyclic aryl groups (e.g., pyridine). The term includes monocyclic or fused-ring polycyclic (i.e., rings which share adjacent pairs of carbon atoms) groups. The term "carbocyclic" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. The term "heteroaromatic" refers to an aromatic group which contains at least one heterocyclic ring.

The term "alkyl," as used herein, means any unbranched or branched, substituted or unsubstituted, saturated hydrocarbon. The alkyl moiety, may be branched, straight chain, or cyclic. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 5 carbon atoms. The alkyl group may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl.

The alkyl group may be substituted or unsubstituted. When substituted, the substituent group(s) is (are) one or more group(s) individually and independently selected from substituted or unsubstituted cycloalkyl, substituted or unsubstituted cycloalkenyl, substituted or unsubstituted aryl, substituted or unsubstituted heteroaryl, substituted or unsubstituted heteroaryloxy, heterocyclyl, heterocyclooxy, heteroalicyclyl, hydroxy, substituted or unsubstituted alkoxy, substituted or unsubstituted aryloxy, acyl, thiol, substituted or unsubstituted thioalkoxy, alkylthio, arylthio, cyano, halo, carbonyl, thiocarbonyl, acylalkyl, acylamino, acyloxy, aminoacyl, aminoacyloxy, oxyacylamino, keto, thioketo, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and substituted or unsubstituted amino, including mono- and di-substituted amino groups, and the protected derivatives thereof, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl and —$SO_2$-heteroaryl. Typical alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. Wherever a substituent is described as being "optionally substituted" that substitutent may be substituted with one of the above substituents.

In the present context, the term "cycloalkyl" is intended to cover three-, four-, five-, six-, seven-, and eight- or more membered rings comprising carbon atoms only. A cycloalkyl can optionally contain one or more unsaturated bonds situated in such a way, however, that an aromatic pi-electron system does not arise. Some examples of "cycloalkyl" are the carbocycles cyclopropane, cyclobutane, cyclopentane, cyclopentene, cyclopentadiene, cyclohexane, cyclohexene, 1,3-cyclohexadiene, 1,4-cyclohexadiene, cycloheptane, or cycloheptene.

An "alkenyl" moiety refers to a group consisting of at least two carbon atoms and at least one carbon-carbon double bond. An alkenyl may be unbranched or branched, substituted or unsubstituted, unsaturated hydrocarbon including polyunsaturated hydrocarbons. In some embodiments, the alkenyl is a $C_1$-$C_6$ unbranched, mono-unsaturated or di-unsaturated, unsubstituted hydrocarbons. The term "cycloalkenyl" refers to any non-aromatic hydrocarbon ring, preferably having five to twelve atoms comprising the ring.

An "alkyne" moiety refers to a group consisting of at least two carbon atoms and at least one carbon-carbon triple bond.

The substituent "R", "R'", or "R''" appearing by itself and without a number designation refers to a substituent selected from the group consisting of hydrogen, alkyl, cycloalkyl, aryl, heteroaryl (bonded through a ring carbon) and heteroalicyclyl (bonded through a ring carbon).

The term "alkoxy" refers to any unbranched, or branched, substituted or unsubstituted, saturated or unsaturated ether, with $C_1$-$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

An "O-carboxy" group refers to a RC(=O)O— group, where R is as defined herein.

A "C-carboxy" group refers to a —C(=O)OR groups where R is as defined herein.

An "acetyl" group refers to a —C(=O)$CH_3$, group.

A "trihalomethanesulfonyl" group refers to a $X_3$CS(=O)$_2$— group where X is a halogen.

A "cyano" group refers to a —CN group.

An "isocyanato" group refers to a —NCO group.

A "thiocyanato" group refers to a —SCN group.

An "isothiocyanato" group refers to a —NCS group.

A "sulfinyl" group refers to a —S(=O)—R group, with R as defined herein.

A "S-sulfonamido" group refers to a —S(=O)$_2$NR, group, with R as defined herein.

A "N-sulfonamido" group refers to a RS(=O)$_2$NH— group with R as defined herein.

A "trihalomethanesulfonamido" group refers to a $X_3$CS(=O)$_2$NR— group with X and R as defined herein.

An "O-carbamyl" group refers to a —OC(=O)—NR, group with R as defined herein.

An "N-carbamyl" group refers to a ROC(=O)NH— group, with R as defined herein.

An "O-thiocarbamyl" group refers to a —OC(=S)—NR, group with R as defined herein.

An "N-thiocarbamyl" group refers to an ROC(=S)NH— group, with R as defined herein.

A "C-amido" group refers to a —C(=O)—NR$_2$ group with R as defined herein.

An "N-amido" group refers to a RC(=O)NR'— group, with R and R' as defined herein.

The term "perhaloalkyl" refers to an alkyl group where all of the hydrogen atoms are replaced by halogen atoms.

The term "acylalkyl" refers to a RC(=O)R— group, with R as defined herein, and R' being a diradical alkylene group. Examples of acylalkyl, without limitation, may include CH$_3$C(=O)CH$_2$—, CH$_3$C(=O)CH$_2$CH$_2$—, CH$_3$CH$_2$C(=O)CH$_2$CH$_2$—, CH$_3$C(=O)CH$_2$CH$_2$CH$_2$—, and the like.

The term "acyloxy" refers to a RC(=O)O— group, with R as defined herein.

The term "alkyloxycarbonyloxy" refers to an alkyl-O—C(=O)O— group.

The term "aryloxycarbonyloxy" refers to an aryl-OC(=O)O— group.

The term "arylalkoxy carbonyl" refers to an aryl-alkoxy (C=O)— group.

The term "aminocarbonyl" refers to an amino(C=O)— group.

The term "aminocarbonyloxy" refers to an amino(C=O)O— group.

Unless otherwise indicated, when a substituent is deemed to be "optionally substituted," it is meant that the substitutent is a group that may be substituted with one or more group(s) individually and independently selected from cycloalkyl, aryl, heteroaryl, heteroalicyclic, hydroxy, alkoxy, aryloxy, mercapto, alkylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives thereof. The protecting groups that may form the protective derivatives of the above substituents are known to those of skill in the art and may be found in references such as Greene and Wuts, above.

The term "heterocyclyl" is intended to mean three-, four-, five-, six-, seven-, and eight- or more membered rings wherein carbon atoms together with from 1 to 3 heteroatoms constitute said ring. A heterocyclyl can optionally contain one or more unsaturated bonds situated in such a way, however, that an aromatic pi-electron system does not arise. The heteroatoms are independently selected from oxygen, sulfur, and nitrogen.

A heterocyclyl can further contain one or more carbonyl or thiocarbonyl functionalities, so as to make the definition include oxo-systems and thio-systems such as lactams, lactones, cyclic imides, cyclic thioimides, cyclic carbamates, and the like.

Heterocyclyl rings can optionally also be fused to aryl rings, such that the definition includes bicyclic structures. Typically such fused heterocyclyl groups share one bond with an optionally substituted benzene ring. Examples of benzo-fused heterocyclyl groups include, but are not limited to, benzimidazolidinone, tetrahydroquinoline, and methylenedioxybenzene ring structures.

Some examples of "heterocyclyls" include, but are not limited to, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Binding to the heterocycle can be at the position of a heteroatom or via a carbon atom of the heterocycle, or, for benzo-fused derivatives, via a carbon of the benzenoid ring.

In the present context the term "aryl" is intended to mean a carbocyclic aromatic ring or ring system. Moreover, the term "aryl" includes fused ring systems wherein at least two aryl rings, or at least one aryl and at least one C$_{3-8}$-cycloalkyl share at least one chemical bond. Some examples of "aryl" rings include optionally substituted phenyl, naphthalenyl, phenanthrenyl, anthracenyl, tetralinyl, fluorenyl, indenyl, and indanyl. The term "aryl" relates to aromatic, including, for example, benzenoid groups, connected via one of the ring-forming carbon atoms, and optionally carrying one or more substituents selected from heterocyclyl, heteroaryl, halo, hydroxy, amino, cyano, nitro, alkylamido, acyl, C$_{1-6}$ alkoxy, C$_{1-6}$ alkyl, C$_{1-6}$ hydroxyalkyl, C$_{1-6}$ aminoalkyl, C$_{1-6}$ alkylamino, alkylsulfenyl, alkylsulfinyl, alkylsulfonyl, sulfamoyl, or trifluoromethyl. The aryl group can be substituted at the para and/or meta positions. In other embodiments, the aryl group can be substituted at the ortho position. Representative examples of aryl groups include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl 3-cyanophenyl, 4-cyanophenyl, dimethylphenyl, naphthyl, hydroxynaphthyl, hydroxymethylphenyl, trifluoromethylphenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

In the present context, the term "heteroaryl" is intended to mean a heterocyclic aromatic group where one or more carbon atoms in an aromatic ring have been replaced with one or more heteroatoms selected from the group comprising nitrogen, sulfur, phosphorous, and oxygen.

Furthermore, in the present context, the term "heteroaryl" comprises fused ring systems wherein at least one aryl ring and at least one heteroaryl ring, at least two heteroaryl rings, at least one heteroaryl ring and at least one heterocyclyl ring, or at least one heteroaryl ring and at least one cycloalkyl ring share at least one chemical bond.

The term "heteroaryl" is understood to relate to aromatic, C$_{3-8}$ cyclic groups further containing one oxygen or sulfur atom or up to four nitrogen atoms, or a combination of one oxygen or sulfur atom with up to two nitrogen atoms, and their substituted as well as benzo- and pyrido-fused derivatives, for example, connected via one of the ring-forming carbon atoms. Heteroaryl groups can carry one or more substituents, selected from halo, hydroxy, amino, cyano, nitro, alkylamido, acyl, C$_{1-6}$-alkoxy, C$_{1-6}$-alkyl, C$_{1-6}$-hydroxyalkyl, C$_{1-6}$-aminoalkyl, C$_{1-6}$-alkylamino, alkylsulfenyl, alkylsulfinyl, alkylsulfonyl, sulfamoyl, or trifluoromethyl. In some embodiments, heteroaryl groups can be five- and six-membered aromatic heterocyclic systems carrying 0, 1, or 2 substituents, which can be the same as or different from one another, selected from the list above. Representative examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quionoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$-alkyl, $C_{1-6}$-alkyl, hydroxy-$C_{1-6}$-alkyl, and amino-$C_{1-6}$-alkyl.

The terms "purified," "substantially purified," and "isolated" as used herein refer to compounds disclosed herein being free of other, dissimilar compounds with which the compounds of the invention are normally associated in their natural state, so that the compounds of the invention comprise at least 0.5%, 1%, 5%, 10%, or 20%, and most preferably at least 50% or 75% of the mass, by weight, of a given sample.

Methods of Preparation

Compounds disclosed herein may be obtained by fermentation of a strain of a marine actinomycete a strain isolated from a marine sediment sample collected at Cocos Lagoon, Guam, a culture of which (also identified as "NPS008920") was deposited on Jan. 19, 2005 with the American Type Culture Collection (ATCC) in Rockville, Md. and assigned the ATCC patent deposition number PTA-6527. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce compounds described herein. Compounds produced by this strain may then be purified.

The production of compounds disclosed herein may be carried out by cultivating the above-identified strain in a suitable nutrient medium under conditions described herein, preferably under submerged aerobic conditions, until a substantial amount of compounds are detected in the fermentation; harvesting by extracting the active components from the mycelial growth with a suitable solvent; concentrating the solution containing the desired components; then subjecting the concentrated material to chromatographic separation to isolate the compounds from other metabolites also present in the cultivation medium.

Production of compounds can be achieved at temperature conducive to satisfactory growth of the producing organism, e.g. from 16 degree C. to 40 degree C., but it is preferable to conduct the fermentation at 22 degree C. to 32 degree C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 300 rpm, preferably at 150 rpm to 250 rpm, for example.

Growth of the microorganisms may be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources may be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cotttonseed meal, fish meal, peptone, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Those of skill in the art will recognize many suitable techniques of fermentation and purification for use in producing compounds disclosed herein. Compounds obtained in this manner may be further modified to generate compounds disclosed herein by semi-synthetic routes. For example, in some embodiments, compounds of formulas Ia, IIIa, IVa, or Va are produced by subjecting compounds of formulas I, III, IV, or V to a suitable ring opening reaction such as by adjusting the pH to a suitable level (e.g., approximately 7.4).

The compounds disclosed herein may also be synthesized by methods described below, or by modification of these methods. Ways of modifying the methodology include, among others, temperature, solvent, reagents etc., and will be obvious to those skilled in the art. In general, during any of the processes for preparation of the compounds disclosed herein, it may be necessary and/or desirable to protect sensitive or reactive groups on any of the molecules concerned. This may be achieved by means of conventional protecting groups, such as those described in *Protective Groups in Organic Chemistry* (ed. J. F. W. McOmie, Plenum Press, 1973); and Greene & Wuts, *Protective Groups in Organic Synthesis*, John Wiley & Sons, 1991, which are both hereby incorporated herein by reference in their entirety. The protecting groups may be removed at a convenient subsequent stage using methods known from the art. Synthetic chemistry transformations useful in synthesizing applicable compounds are known in the art and include e.g. those described in R. Larock, *Comprehensive Organic Transformations*, VCH Publishers, 1989, or L. Paquette, ed., *Encyclopedia of Reagents for Organic Synthesis*, John Wiley and Sons, 1995, which are both hereby incorporated herein by reference in their entirety.

Compounds described herein can be synthesized by the synthetic scheme A:

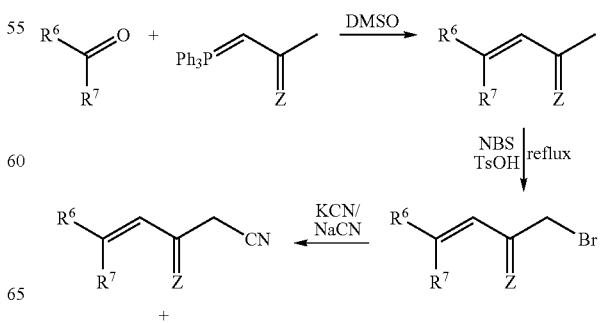

Scheme A

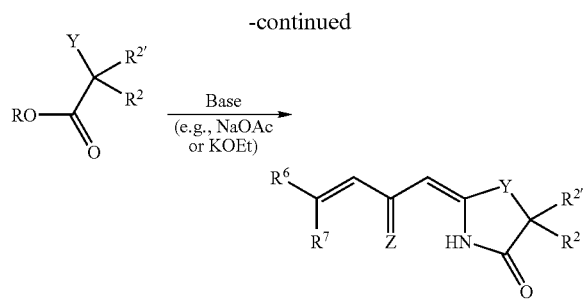

In Scheme A, $R^2$, $R^{2'}$, $R^6$, $R^7$, Y, and Z are as described above for formulas I, III, and IV. R may be hydrogen or a strait or branched chain $C_{1-6}$ alkyl.

Where the processes for the preparation of the compounds disclosed herein give rise to mixtures of stereoisomers, such isomers may be separated by conventional techniques such as preparative chiral chromatography. The compounds may be prepared in racemic form or individual enantiomers may be prepared by stereoselective synthesis or by resolution. The compounds may be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved using a chiral auxiliary by formation of diastereomeric derivatives such as esters, amides or ketals followed by chromatographic separation and removal of the chiral auxiliary.

Methods of Use

In some embodiments, the compounds described herein can be used for the treatment of cancer and/or microbial infection. Thus, for example, the compounds described herein can be used to treat, prevent the formation of, slow the growth of, or kill cancer cells. In some embodiments, the compounds described herein are administered to a subject suffering from cancer. In one embodiment, the subject is a human. In some embodiments, cancer cells are contacted with one or more of the compounds described herein. In one embodiment, the cancer is a melanoma.

In some embodiments, the compounds described herein can be used to treat a bacterial infection. In some embodiments, the compounds prevent the formation of, slow the growth of, or kill bacteria. In some embodiments, the compounds described herein are administered to a subject suffering from a bacterial infection. In one embodiment, the subject is a human. In some embodiments, bacteria are contacted with one or more compounds described herein. In some embodiments, the bacteria are Gram-positive bacteria. In one embodiment, the bacteria is *Staphylococcus aureus* (methicillin sensitive), *Staphylococcus aureus* (methicillin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), or *Enterococcus faecium* (vancomycin resistant). In some embodiments, the Gram-negative bacteria is *Haemophilus influenzae*.

Pharmaceutical Compositions

In another aspect, the present disclosure relates to a pharmaceutical composition comprising a physiologically acceptable surface active agents, carriers, diluents, excipients, smoothing agents, suspension agents, film forming substances, and coating assistants, or a combination thereof; and a compound disclosed herein. Acceptable carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or carriers. The pharmaceutical composition facilitates administration of the compound to an organism. Multiple techniques of administering a compound exist in the art including, but not limited to, oral, injection, aerosol, parenteral, and topical administration. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism.

The term "diluent" defines chemical compounds diluted in water that will dissolve the compound of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

The term "physiologically acceptable" defines a carrier or diluent that does not abrogate the biological activity and properties of the compound.

The pharmaceutical compositions described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compounds can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations (for example, liposomes), may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Pharmaceutical compositions for intraocular delivery include aqueous ophthalmic solutions of the active compounds in water-soluble form, such as eyedrops, or in gellan gum (Shedden et al., *Clin. Ther.*, 23(3):440-50 (2001)) or hydrogels (Mayer et al., *Opthalmologica*, 210(2):101-3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29-45 (1994)), lipid-soluble formulations (Alm et al., *Prog. Clin. Biol. Res.*, 312:447-58 (1989)), and microspheres (Mordenti, *Toxicol. Sci.*, 52(1): 101-6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Agents intended to be administered intracellularly may be administered using techniques well known to those of ordinary skill in the art. For example, such agents may be encapsulated into liposomes. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. The liposome may be coated with a tissue-specific antibody. The liposomes will be targeted to and taken up selectively by the desired organ. Alternatively, small hydrophobic organic molecules may be directly administered intracellularly.

Additional therapeutic or diagnostic agents may be incorporated into the pharmaceutical compositions. Alternatively or additionally, pharmaceutical compositions may be combined with other compositions that contain other therapeutic or diagnostic agents.

Methods of Administration

The compounds or pharmaceutical compositions may be administered to the patient by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; (d) administration locally such as by injection directly in the renal or cardiac area, e.g., by depot implantation; as well as (e) administration topically; as deemed appropriate by those of skill in the art for bringing the compound of the invention into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al., 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are between about 0.1% and 500%, more preferably between about 25% and 250% of the established human dosage. Where no human dosage is established, as will be the case for newly-discovered pharmaceutical compounds, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of between 0.1 mg and 2000 mg of each active ingredient, preferably between 1 mg and 500 mg, e.g. 5 to 200 mg. In other embodiments, an intravenous, subcutaneous, or intramuscular dose of each active ingredient of between 0.01 mg and 100 mg, preferably between 0.1 mg and 60 mg, e.g. 1 to 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition, including but not limited to cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

EXAMPLES

Example 1

Fermentation of NPS-008920

Strain NPS008920 was grown in a 40 ml tube containing 10 ml of seed medium consisting of the following per liter of sea water: starch, 10 g; yeast extract, 4 g; and peptone, 2 g. The culture was allowed to incubate for 3 days at 28 degree C. on a rotary shaker operating at 250 rpm. The vegetative culture was mixed with 2 ml of cryoprotective solution consisting of 500 g glycerol per liter of deionized water. 1.5 ml portions of this mixture were transferred to sterile cryogenic tube (1.8 ml capacity). The vegetative cultures so obtained were frozen and stored at −80 degree C.

Seed culture was prepared by transferring two 1.5 ml of the cryopreservative cultures to a 100 ml flask containing 100 ml of sterile seed medium having the same composition as the above. The seed culture was incubated at 28 degrees C. for 4 days on a rotary shaker operating at 250 rpm. Five ml of this seed culture was inoculated into nine 500 ml flasks each containing 100 ml of the seed medium. The second seed cultures were incubated at 28 degrees C. for 2 days on a rotary shaker operating at 250 rpm. Five to six ml each of the second seed culture was inoculated into the production medium having the same composition of the seed medium. The production culture was incubated at 28 degree C. for 5 days on a rotary shaker operating at 250 rpm. The culture broth (5 L) was extracted with 5 liters of ethyl acetate. The extract was dried in vacuo.

Example 2

Purification to Obtain Compounds of Formulae VI and VII

The crude extract (0.38 g) of NPS008920 obtained as described in Example 1 was dissolved in MeOH (19 ml) and injected in 950 µl aliquots (19 mg each) on preparative reversed phase HPLC using the following conditions:

Column: Ace 5 um C18-HL
Dimensions: 15 cm×21 mm ID
Flow rate: 14.5 ml/min
Detection: UV DAD
Solvent: 20% ACN/$H_2O$ to 80% ACN/$H_2O$ in 12 min; 80% to 100% ACN/$H_2O$ in 1 min then 9 min at 100% ACN Two compounds were well separated using the above conditions. One compound (identified as the compound of formula VI) eluted at 21 minutes. The second compound (identified as the compound of formula VII) eluted at 23 minutes. These compounds were further purified by reversed phase semi-preparative HPLC using the following conditions:

Column: Hamilton 10 um PRP-1 (Polymeric Reversed Phase)
Dimensions: 25 cm×10 mm ID
Flow rate: 3 ml/min
Detection: UV DAD
Solvent: Gradient of 40% ACN/$H_2O$ to 80% ACN/$H_2O$ in 8 min; 80% to 100% ACN in 1 min then 15 min at 100% ACN.

Example 3

Fermentation of NPS-008920

Strain NPS008920 was grown in a 100 ml flask containing 100 ml of seed medium consisting of the following per liter of sea water: starch, 10 g; yeast extract, 4 g; and peptone, 2 g. The culture was allowed to incubate for 6 days at 28 degree C. on a rotary shaker operating at 250 rpm. The vegetative culture was mixed with cryoprotective solution consisting of 500 g glycerol per liter of deionized water to yield a final glycerol concentration of 10%. 1.5 ml portions of this mixture were transferred to sterile cryogenic tube (1.8 ml capacity). The vegetative cultures so obtained were frozen and stored at −80 degree C.

Seed culture was prepared by transferring two 1.5 ml of the cryopreservative cultures to a 100 ml flask containing 100 ml of sterile seed medium having the same composition as the above. The seed culture was incubated at 28 degrees C. for 3 days on a rotary shaker operating at 250 rpm. Five ml of this seed culture was inoculated into nine 500 ml flasks each containing 100 ml of the seed medium. The second seed cultures were incubated at 28 degrees C. for 2 days on a rotary shaker operating at 250 rpm. Five to six ml each of the second seed culture was inoculated into the production medium having the same composition of the seed medium. The production culture was incubated at 28 degree C. for 5 days on a rotary shaker operating at 250 rpm. The culture broth (10 L) was extracted with 10 liters of ethyl acetate. The extract was dried in vacuo.

Example 4

Purification to Obtain the Compound of Formula VIII

The crude extract (1.2 g) of NPS008920 obtained as described in Example 3 was dissolved in water (100 mL) and extracted with hexane (3×100 mL). The combined organic layer was concentrated to yield about 570 mg of Formula VI enriched material which was purified by preparative scale reversed phase HPLC using the following conditions (~50 mg per injection).

Column: Ace 5 um C18-HL
Dimensions: 15 cm×21 mm ID
Flow rate: 14.5 ml/min
Detection: UV DAD
Solvent: 50% ACN/$H_2O$ to 100% ACN in 12 min; then 13 min at 100% ACN The compound of formula VIII eluted at about 18 min as a minor compound. This compound was further purified by reversed phase preparative HPLC using the following conditions with different solvent system:

Column: Ace 5 um C18-HL
Dimensions: 15 cm×21 mm ID
Flow rate: 14.5 ml/min
Detection: UV DAD
Solvent: 20% MeOH/$H_2O$ to 80% MeOH/$H_2O$ in 12 min; 80% to 100% MeOH/$H_2O$ in 1 min then 9 min at 100% MeOH The pure compound of formula VIII was eluted at about 18.5 min.

Example 5

Preparation of the Compound of Formula IX

The compound of formula IX was obtained by adding pH 7.4 buffer (2 mL) into a solution of the compound of formula XIII (4.2 mg) in acetonitrile and letting it stand at room temperature for about 4 days. The acetonitrile was removed by rotavap and the remaining aqueous layer was extracted with methyl chloride (3×20 mL). The combined organic layer was concentrated to yield the compound of formula IX (3.2 mg).

Example 6

Structural Characterization

The compounds of Formulas VI, VII, VIII, and IX were characterized as follows:

$[\alpha]^{21.2}{}_D$ −30.99 (c 0.0002, MeOH); UV (MeOH) $\lambda_{max}$ 310 (ε22,700), 253 (9,100) nm; UV (Acetonitrile/H$_2$O) $\lambda_{max}$ 310, 255 nm. HRESIMS m/z 322.2372 [M+H] $\Delta_{calc}$ C$_{19}$H$_{32}$NO$_3$ (322.2382)=3.3 ppm.     Formula VI UV (Acetonitrile/H$_2$O) $\lambda_{max}$ 310, 255 nm. HRESIMS m/z 336.2527 [M+H] $\Delta_{calc}$ C$_{20}$H$_{34}$NO$_3$ (336.2539)=3.5 ppm.     Formula VII UV (Acetonitrile/H$_2$O) $\lambda_{max}$ 310, 255 nm. HRESIMS m/z 308.2234 [M+H] $\Delta_{calc}$ C$_{18}$H$_{30}$NO$_3$ (308.2226)=2.8 ppm.     Formula VIII UV (Acetonitrile/H$_2$O) $\lambda_{ax}$ 245 nm. LRESIMS m/z 340 [M+H].     Formula IX $^1$H-NMR and $^{13}$C-NMR was conducted in order to elucidate the structures of the four compounds. The results are indicated in Tables 1-4 and the assignments were made as illustrated in the following structures:

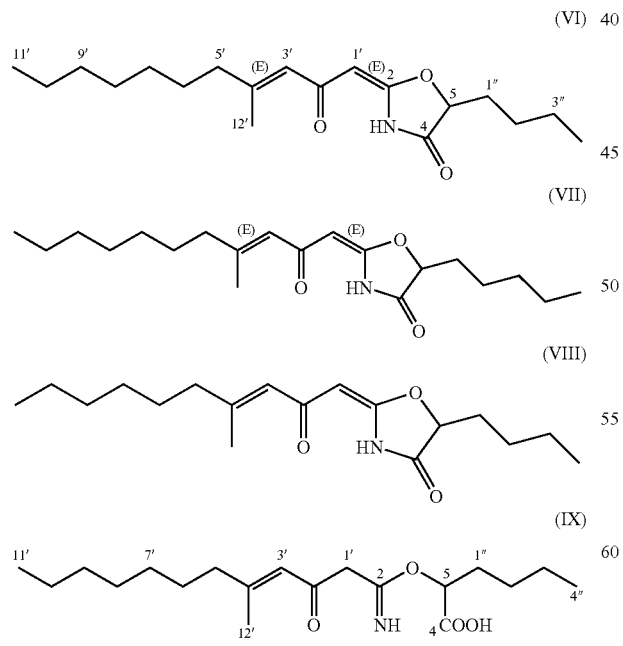

The double bond geometry of C-1' to C-2 was not established for Formulae VI, VII and VIII.

TABLE 1

$^1$H NMR Assignments.

| | Formula VI | | Formula VII CDCl$_3$ |
|---|---|---|---|
| | DMSO-d6 | CDCl$_3$ | |
| Pos | *$\delta_H$ int., mult, J (Hz) | **$\delta_H$ int., mult, J (Hz) | **$\delta_H$ int., mult, J (Hz) |
| 5 | 4.88 1H, dd, 4.7, 6.6 | 4.59 1H, dd, 4.4, 7.0 | 4.58 1H, dd, 4.4, 7.0 |
| 1' | 5.28 1H, s | 5.18 1H, s | 5.17 1H, s |
| 3' | 5.98 1H, br s | 5.87 1H, br s | 5.86 1H, br s |
| 5' | 2.08 2H, br t, 7.5 | 2.10 3H, br t, 7.6 | 2.09 2H, br t, 7.6 |
| 6' | 1.43 2H, m | 1.44 2H, m | 1.44 2H, m |
| 7' | 1.25 2H, ca | 1.26 2H, m | 1.26 2H, m |
| 8' | 1.25 2H, ca | 1.26 2H, m | 1.26 2H, m |
| 9' | 1.25 2H, ca | 1.23 2H, m | 1.23 2H, m |
| 10' | 1.28 2H, ca | 1.26 2H, m | 1.26 2H, m |
| 11' | 0.86 3H, t, 6.6 | 0.87 3H, t, 7.0 | 0.85 3H, t, 7.0 |
| 12' | 2.11 3H, br s | 2.15 3H, br s | 2.14 3H, br s |
| 1" | 1.71 1H, m | 1.79 1H, m | 1.77 1H, m |
| | 1.84 1H, m | 1.96 1H, m | 1.94 1H, m |
| 2" | 1.31 2H, ca | 1.40 2H, m | 1.42 2H, m |
| 3" | 1.30 2H, ca | 1.36 2H, m | 1.28 2H, m |
| 4" | 0.87 3H, t, 6.6 | 0.90 3H, t, 7.0 | 1.28 2H, m |
| 5" | — | — | 0.86 3H, t, 7.0 |

*$\delta_H$ values referenced to internal solvent for DMSO-d$_6$ at 2.50 ppm
**$\delta_H$ values referenced to internal solvent for CDCl$_3$ at 7.24 ppm

TABLE 2

$^1$H NMR Assignments.

| | Formula VIII CDCl$_3$ | Formula IX CDCl$_3$ |
|---|---|---|
| Pos | *$\delta_H$ int., mult, J (Hz) | *$\delta_H$ int., mult, J (Hz) |
| 5 | 4.59 1H, dd, 4.4, 7.0 | 5.24 1H, dd, 3.8, 8.5 |
| 1' | 5.18 1H, s | 3.56 1H, d, 16.4 |
| | | 3.67 1H, d, 16.4 |
| 3' | 5.87 1H, br s | 6.02 1H, br s |
| 5' | 2.10 3H, br t, 7.6 | 2.15 2H, br t, 7.6 |
| 6' | 1.44 2H, m | 1.46 2H, m |
| 7' | 1.28 2H, m | 1.26 2H, m |
| 8' | 1.24 2H, m | 1.26 2H, m |
| 9' | 1.27 2H, m | 1.23 2H, m |
| 10' | 0.86 3H, t, 7.0 | 1.26 2H, m |
| 11' | — | 0.87 3H, t, 7.0 |
| 12' | 2.15 3H, br s | 2.15 3H, br s |
| 1" | 1.79 1H, m | 1.82 1H, m |
| | 1.96 1H, m | 1.96 1H, m |
| 2" | 1.41 2H, m | 1.34 2H, m |
| 3" | 1.35 2H, m | 1.31 2H, m |
| 4" | 0.90 3H, t, 7.0 | 0.88 3H, t, 7.0 |

*$\delta_H$ values referenced to internal solvent for CDCl$_3$ at 7.24 ppm

TABLE 3

13C NMR Assignments.

| | Formula VI | | Formula VII |
|---|---|---|---|
| Pos | $\delta_C$* mult in DMSO | $\delta_C$** mult in CDCl$_3$ | $\delta_C$** mult in CDCl$_3$ |
| 2 | 165.3 s | 166.7 s | 166.5 s |
| 4 | 173.8 s | 173.7 s | 173.6 s |
| 5 | 77.6 d | 78.6 d | 78.6 d |
| 1' | 83.6 d | 84.0 d | 84.0 d |
| 2' | 187.9 s | 189.4 s | 189.4 s |
| 3' | 124.6 d | 124.3 d | 124.3 d |
| 4' | 155.4 s | 157.7 s | 157.7 s |
| 5' | 40.4 t | 41.5 t | 41.4 t |
| 6' | 27.0 t | 27.6 t | 27.6 t |
| 7' | 28.4 t | 29.1 t$^e$ | 29.1 t$^d$ |
| 8' | 28.6 t | 29.2 t$^e$ | 29.7 t$^d$ |
| 9' | 31.1 t | 31.8 t | 31.7 t |
| 10' | 22.0 t | 22.6 t | 22.6 t |
| 11' | 13.9 q | 14.1 q | 14.0 q |
| 12' | 18.4 q | 19.2 q | 19.1 q |
| 1" | 29.9 t | 30.8 t | 31.0 t |
| 2" | 25.6 t | 26.2 t | 23.7 t |
| 3" | 21.6 t | 22.2 t | 31.2 t |
| 4" | 13.6 q | 13.7 t | 22.3 t |
| 5" | — | — | 13.9 q |

*$\delta_C$ values referenced to internal solvent for DMSO-d$_6$ at 39.50 ppm
**$\delta_C$ values referenced to internal solvent for CDCl$_3$ at 77.00 ppm (some values obtained through HMBC and HMQC)
$^{d,e}$may be interchangeable

TABLE 4

13C NMR Assignments.

| | Formula VIII $\delta_C$** mult in CDCl$_3$ | Formula IX $\delta_C$** mult in CDCl$_3$ |
|---|---|---|
| Pos | | |
| 2 | 166.6 s | 166.6 s |
| 4 | 173.7 s | 172.8 s |
| 5 | 78.6 d | 74.3 d |
| 1' | 84.1 d | 50.3 t |
| 2' | 189.4 s | 193.5 s |
| 3' | 124.3 d | 121.5 d |
| 4' | 157.7 s | 164.9 s |
| 5' | 41.5 t | 41.5 t |
| 6' | 27.6 t | 27.5 t |
| 7' | 28.9 t | 29.0 t$^a$ |
| 8' | 31.7 t | 29.2 t$^a$ |
| 9' | 22.5 t | 31.7 t |
| 10' | 14.0 q | 22.6 t |
| 11' | — | 14.0 q$^b$ |
| 12' | 19.1 q | 20.0 q |
| 1" | 30.8 t | 31.2 t |
| 2" | 26.1 t | 27.2 t |
| 3" | 22.2 t | 22.3 t |
| 4" | 13.7 q | 13.9 q$^b$ |

**$\delta_C$ values referenced to internal solvent for CDCl$_3$ at 77.00 ppm
$^{a,b}$may be interchangeable Example 7

Growth Inhibition of Murine Melanoma, B16-F10 Cells

B16-F10 (ATCC; CRL-6475) a murine melanoma cell line was maintained in complete Dulbecco's Modification of Eagle's Medium (DMEM) (DMEM supplemented with 10% (v/v) Fetal bovine serum, 2 mM glutamine, 10 mM HEPES and Penicillin/Streptomycin at 100 IU/ml and 100 µg/ml respectively). The cells were cultured in an incubator at 37° C. in 5% $CO_2$ and 95% humidified air.

For cell growth inhibition assays, B16-F10 cells were seeded at $1.25 \times 10^3$ cells/well in 90 µl complete media into Corning 3904 black-walled, clear-bottom tissue culture plates and the plates were incubated overnight to allow cells to establish and enter log phase growth. 20 mM stock solutions of formula VI were prepared in 100% DMSO. 10× concentrated serial dilutions of formula VI were prepared in complete media. Ten µl volumes of the serial dilutions were added to the test wells in triplicate resulting in final concentrations ranging from 20 µM to 6.32 nM. The plates were returned to the incubator for 48 hours. The final concentration of DMSO was 0.25% in all samples.

Following 48 hours of drug exposure, 10 µl of 0.2 mg/ml resazurin (obtained from Sigma-Aldrich Chemical Co.) in $Mg^{2+}$, $Ca^{2+}$ free phosphate buffered saline was added to each well and the plates were returned to the incubator for 3-6 hours. Since living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. Resazurin dye in medium without cells was used to determine the background, which was subtracted from the data for all experimental wells. The data were normalized to the average fluorescence of the cells treated with media +0.25% DMSO (100% cell growth) and $EC_{50}$ values (the drug concentration at which 50% of the maximal observed growth inhibition is established) were determined using a standard sigmoidal dose response curve fitting algorithm (XLfit 3.0, ID Business Solutions Ltd).

The data in Table 5 summarize the mean growth inhibitory effects of the compound of formula VI against the murine melanoma, B16-F10 cell line.

TABLE 5

$EC_{50}$ values of formula V against B16-F10 cells.

| FORMULA VI | B16-F10 |
|---|---|
| $EC_{50}$ (µM) | 6.0 ± 2.6* |

*data presented as mean ± standard deviation of three independent experiments

The $EC_{50}$ value indicates that the compound of formula VI inhibits the growth of B16-F10 tumor cells.

Example 8

Antimicrobial Assays

Minimum inhibitory concentrations (MICs) were determined according to the National Committee for Clinical Laboratory Standards (NCCLS) susceptibility test guideline M7-A5 (Ferraro, M. 2001 Methods for Dilution Antimicrobial Susceptibility Tests for Bacteria that Grow Aerobically; Approved Standard (NCCLS). National Committee for Clinical Laboratory Standards (NCCLS), Villanova, which is incorporated herein by reference in its entirety). The compound of formula VI was tested in DMSO while the compound of formula VII was tested in aqueous MeOH. Antimicrobial data for the compounds of formulae VI and VII are shown in Table 6. The compound of formulae VIII and IX were tested in DMSO. Antimicrobial data for the compounds of formulae VIII and IX are shown in Table 7.

TABLE 6

Antimicrobial data.

| Organism | MIC (µg/ml) | |
|---|---|---|
| | Formula VI | Formula VII |
| *Staphylococcus aureus* - MSSA | 0.88 | 6 |
| *Staphylococcus aureus* - MRSA | 1.04 | 1.5 |
| *S. epi.* 700578 | 0.54 | 1.25 |
| *S. epi.* 700582 | 0.54 | 0.75 |
| PSSP | 2.58 | 8 |
| PRSP | 4.67 | 6 |
| VSE | 3.67 | 3 |
| VRE | 1.83 | 1.5 |
| *E. c.* imp | >32 | >32 |
| *E. c.* MCR106 | >32 | >32 |
| *E. c.* 25922 | >32 | >32 |
| *H. inf.* 49247 | 12 | 12 |
| *H. inf.* 49766 | 12 | 16 |
| *Candida albicans* | >32 | >32 |

TABLE 7

Antimicrobial data.

| Organism | MIC (µg/ml) | |
|---|---|---|
| | Formula VIII | Formula IX |
| *Staphylococcus aureus* - MSSA | 4 | 24 |
| *Staphylococcus aureus* - MRSA | 3 | >32 |
| PSSP | 10 | >32 |
| *H. inf.* 49247 | 16 | >32 |
| *H. inf.* 49766 | 5 | >32 |

The compounds of formulas VI, VII, and VIII were shown to possess anti-bacterial activity versus the Gram-positive microorganisms tested and were also weakly active against the Gram-negative microorganism *Haemophilus influenzae*.

What is claimed is:

1. A method of treating an individual infected with a bacterium, comprising: administering to the individual a compound having the structure of formula I:

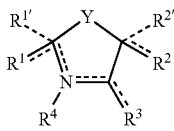

(I)

and pharmaceutically acceptable salts or prodrugs thereof, wherein:

$R^1$ and $R^2$ are separately selected, wherein one of $R^1$ and $R^2$ is a molecular fragment having the structure of formula (II),

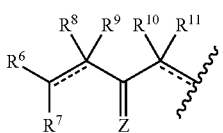

(II)

Z is selected from the group consisting of O, S, and $NR^5$;
$R^6$ and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^8$ and $R^9$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; and halogenated alkyl including polyhalogenated alkyl; or are separately absent;

$R^{10}$ and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

and the remaining substituent of $R^1$ and $R^2$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; heteroaryl; ester; arylalkoxy carbonyl; alkoxy carbonylacyl; amino; aminocarbonyl; amide; aminocarbonyloxy; nitro; azido; hydroxy; alkylthio; arylthio; oxysulfonyl; carboxy; cyano; and halogenated alkyl including polyhalogenated alkyl;

$R^3$ is =O;

$R^{1'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy;

cycloalkoxy; heteroaryl; ester; arylalkoxy carbonyl; alkoxy carbonylacyl; amino; aminocarbonyl; amide; aminocarbonyloxy; nitro; azido; hydroxy; alkylthio; arylthio; oxysulfonyl; carboxy; cyano; and halogenated alkyl including polyhalogenated alkyl; or are separately absent;

Y is separately selected from the group consisting of O, S, and $NR^5$;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl, or are separately absent;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

2. The method of claim 1, wherein the bacterium is a Gram-positive bacterium.

3. The method of claim 1, wherein the bacterium is selected from one or more of *Staphylococcus aureus* (methicillin sensitive), *Staphylococcus aureus* (methicillin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and *Haemophilus influenzae*.

4. The method of claim 1, wherein the compound has the structure of formula VI, wherein the crossed double bond indicates that the double bond may have either trans or cis geometry:

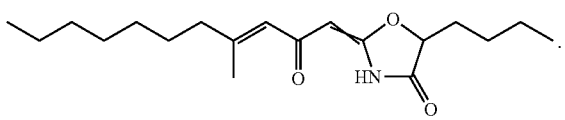

(VI)

5. The method of claim 1, wherein the compound has the structure of formula VII, wherein the crossed double bond indicates that the double bond may have either trans or cis geometry:

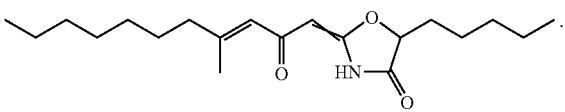

(VII)

6. The method of claim 1, wherein the compound has the structure of formula VIII, wherein the crossed double bond indicates that the double bond may have either trans or cis geometry:

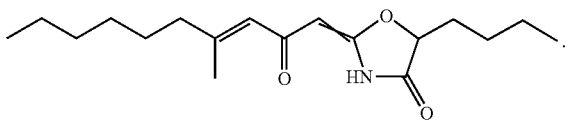

(VIII)

7. A method of treating an individual infected with a bacterium, comprising: administering to the individual a compound having the structure of formula III:

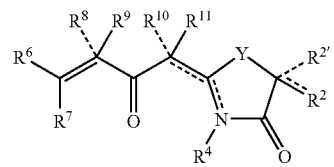

(III)

and pharmaceutically acceptable salts or prodrugs thereof, wherein:

Y is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent;

$R^8$, $R^9$, $R^{10}$, and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

8. The method of claim 7, wherein the bacterium is a Gram-positive bacterium.

9. The method of claim 7, wherein the bacterium is selected from one or more of *Staphylococcus aureus* (methicillin sensitive), *Staphylococcus aureus* (methicillin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and *Haemophilus influenzae*.

10. A method of treating an individual infected with a bacterium, comprising: administering to the individual compound having the structure of formula IV:

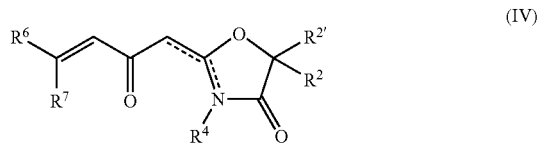

(IV)

and pharmaceutically acceptable salts or prodrugs thereof, wherein:

$R^2$, $R^6$, and $R^7$ are separately selected from the group consisting of mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl;

$R^{2'}$ is selected from the group consisting of hydrogen and mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl;

$R^4$ is selected from the group consisting of hydrogen, straight- or branched-chain $C_{1-6}$ alkyl, straight- or branched-chain $C_{2-6}$ alkenyl, and straight- or branched-chain $C_{2-6}$ alkynyl, or is absent;

any bond represented by a dashed and solid line represents a bond selected from the group consisting of a single bond and a double bond with the proviso that such bonds in the compound of formula IV may not both be double bonds; and any carbon-carbon double bond has a configuration selected from the group consisting of cis and trans.

11. The method of claim 10, wherein the bacterium is a Gram-positive bacterium.

12. The method of claim 10, wherein the bacterium is selected from one or more of *Staphylococcus aureus* (methicillin sensitive), *Staphylococcus aureus* (methicillin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and *Haemophilus influenzae*.

13. A method of treating an individual infected with a bacterium, comprising: administering to the individual a compound having the structure of formula V:

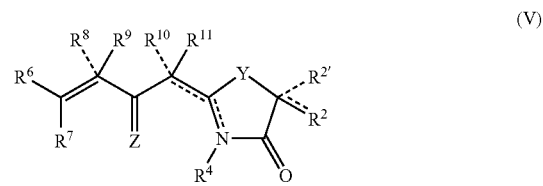

(V)

and pharmaceutically acceptable salts or prodrugs thereof, wherein:

Y is selected from the group consisting of O and $NR^5$;

Z is selected from the group consisting of O, S, and $NR^5$;

$R^2$, $R^6$, and $R^7$ are separately selected from the group consisting of hydrogen;

halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent;

$R^8$ and $R^9$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; and halogenated alkyl including polyhalogenated alkyl; or are separately absent;

$R^{10}$ and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

$R^6$ and $R^8$ are optionally bound together to form an optionally substituted ring;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

14. The method of claim 13, wherein the bacterium is a Gram-positive bacterium.

15. The method of claim 13, wherein the bacterium is selected from one or more of *Staphylococcus aureus* (methicillin sensitive), *Staphylococcus aureus* (methicillin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and *Haemophilus influenzae*.

16. A method of treating an individual infected with a bacterium, comprising: administering to the individual a compound having the structure of formula V:

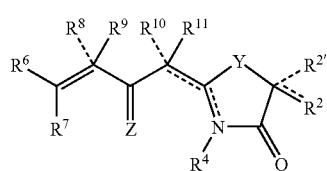

and pharmaceutically acceptable salts or prodrugs thereof, wherein:

Y is selected from the group consisting of O, S, and $NR^5$;

Z is selected from the group consisting of O, S, and $NR^5$;

$R^2$, $R^6$, and $R^7$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl;

$R^{2'}$ is selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or is absent;

$R^4$ and each $R^5$ are separately selected from the group consisting of hydrogen; mono-substituted, poly-substituted or unsubstituted, straight or branched chain variants of the following residues: $C_{1-6}$ alkyl, $C_{2-6}$ alkenyl, $C_{2-6}$ alkynyl, $C_{2-6}$ heteroalkyl, $C_{2-6}$ aminoalkyl, $C_{2-6}$ haloalkyl, $C_{1-6}$ alkoxycarbonyl, and $C_{2-6}$ hydroxyalkyl; $C_{3-8}$ cycloalkyl; —C(O)—$C_{5-6}$ aryl substituted with $C_{1-3}$ alkyl or halo; $C_{5-6}$ aryl; $C_{5-6}$ heteroaryl; $C_{5-6}$ cycloalkyl; and $C_{5-6}$ heterocycloalkyl or are separately absent;

$R^8$ and $R^9$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; amino; aminocarbonyl; amide; aminocarbonyloxy; nitro; azido; phenyl; hydroxy; alkylthio; arylthio; oxysulfonyl; carboxy; and halogenated alkyl including polyhalogenated alkyl; or are separately absent;

$R^{10}$ and $R^{11}$ are separately selected from the group consisting of hydrogen; halogen; mono-substituted, poly-substituted or unsubstituted, straight or branched chain variants of the following residues: $C_1$-$C_{24}$ alkyl, $C_2$-$C_{24}$ alkenyl, or $C_2$-$C_{24}$ alkynyl; acyl; acyloxy; alkyloxycarbonyloxy; aryloxycarbonyloxy; cycloalkyl; cycloalkenyl; alkoxy; cycloalkoxy; aryl; heteroaryl; heterocycloalkyl; ester; arylalkoxy carbonyl; alkoxy carbonylacyl; amino; aminocarbonyl; amide; aminocarbonyloxy; nitro; azido; phenyl; hydroxy; alkylthio; arylthio; oxysulfonyl; carboxy; cyano; and halogenated alkyl including polyhalogenated alkyl; or are separately absent;

$R^6$ and $R^8$ are optionally bound together to form an optionally substituted ring, provided that if $R^6$ and $R^8$ together form an aryl, then at least one of $R^2$, $R^4$, and $R^{11}$ is not hydrogen;

any bond represented by a dashed and solid line represents a bond selected from the group consisting of a single bond and a double bond;

any bond represented by a single dashed line is a single bond or is absent; and any carbon-carbon double bond has a configuration selected from the group consisting of cis and trans.

17. The method of claim 16, wherein the bacterium is a Gram-positive bacterium.

18. The method of claim 16, wherein the bacterium is selected from one or more of *Staphylococcus aureus* (methicillin sensitive), *Staphylococcus aureus* (methicillin resistant), *Streptococcus pneumonia* (penicillin sensitive), *Streptococcus pneumonia* (penicillin resistant), *Staphylococcus epidermis* (multiple drug resistant), *Enterococcus faecalis* (vancomycin sensitive), *Enterococcus faecium* (vancomycin resistant), and *Haemophilus influenzae*.

* * * * *